United States Patent [19]

Warm et al.

[11] Patent Number: 4,983,744

[45] Date of Patent: Jan. 8, 1991

[54] SUBSTITUTED THIENYLETHYLAMINES AND PROCESS FOR THEIR PRODUCTION

[75] Inventors: Aleksander Warm; John McGarrity, both of Visp, Switzerland

[73] Assignee: Lonza Ltd., Gampel/Valais, Switzerland

[21] Appl. No.: 469,354

[22] Filed: Jan. 24, 1990

Related U.S. Application Data

[62] Division of Ser. No. 07/418,340, Oct. 6, 1989.

[30] Foreign Application Priority Data

Oct. 11, 1988 [CH] Switzerland .......................... 3795/88

[51] Int. Cl.$^5$ .................. C07D 333/12; C07D 333/22
[52] U.S. Cl. ........................ 549/75; 549/76; 549/77
[58] Field of Search .............................. 549/75, 76, 77

[56] References Cited

U.S. PATENT DOCUMENTS 4,051,141 9/1977 Castaigne .
4,127,580 11/1978 Braye .
4,870,076 9/1989 Heckel et al. .

OTHER PUBLICATIONS

The Merck Index, 10th Ed., (1983), p. 9274.
E. Saltiel et al., Drugs, 34, (1987), pp. 222–262.

*Primary Examiner*—Alan Siegel
*Attorney, Agent, or Firm*—Fisher, Christen & Sabol

[57] ABSTRACT

Substituted thienylethylamines of the formula:

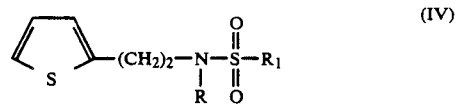

wherein R is formyl, acetyl or benzoyl or is benzyl, which is ring-substituted by at least one halogen atom, and $R_1$ is lower alkyl, phenyl or substituted phenyl, are initial products for the production of antithromobolytically-effective pharmaceutical agents. A process for the production of the above-mentioned compounds from substituted ethanolamines by their reaction with strong bases, further reaction with the resultant aziridines with 2-thienyllithium, and conversion of the resultant thienylethylamines with compounds of formula RX, wherein R has the above-mentioned meaning and X is a halogen.

6 Claims, No Drawings

SUBSTITUTED THIENYLETHYLAMINES AND PROCESS FOR THEIR PRODUCTION

This is a divisional of application Ser. No. 418,340, of Aleksander WARM et al., filed on Oct. 6, 1989.

FIELD OF THE INVENTION

The invention relates to substituted thienylethylamines of the formula:

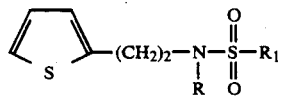
(IV)

wherein R is formyl, acetyl or benzoyl or is benzyl, which is ring-substituted by at least one halogen atom, and $R_1$ is lower alkyl, phenyl or substituted phenyl, as well as a process for the production of the new compounds.

BROAD DESCRIPTION OF THE INVENTION

Objects of the invention are to provide such substituted thienylethylamines and to provide a process for preparing such substituted thienylethylamines.

The invention involves substituted thienylethylamines of the formula:

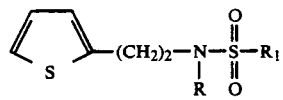
(IV)

wherein R is formyl, acetyl or benzoyl or is benzyl, which is ring-substituted by at least one halogen atom, and $R_1$ is lower alkyl, phenyl or substituted phenyl, as well as a process for the production of the new compounds. Such substituted thienylethylamines can be used as intermediate products for the production of antithrombolytically effective 4,5,6,7-tetrahydro-thieno-[3,2c] pyridines [E. Saltiel et al., Drugs, 34 (1987), pp. 222 to 262].

Substituted ethanolamines of the formula:

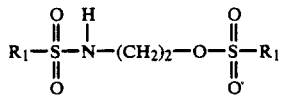
(I)

as starting compounds in the process according to the invention are easily accessible from ethanolamine by its reaction with two equivalents of the corresponding halide:

(V)

wherein $R_1$ has the above-mentioned meaning and X is chlorine, bromine or iodine.

Conversion of substituted ethanolamine I to aziridine II of the formula:

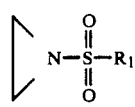
(II)

wherein $R_1$ has the above-mentioned meaning, is achieved with a strong base in the presence of an inert solvent. Alkali hydrides, alkali amides or alkyllithium, known in the trade and representative, can suitably be used as the strong base. Preferably alkali hydrides, such as, sodium hydride, are used. Ethers, such as, tetrahydrofuran, diethyl ether, dimethoxyethane or butylmethyl ether, are suitably used as the inert solvent. The reaction temperature advantageously varies between −80° and +100° C., especially advantageously between 0° and +20° C.

The resultant aziridine can be isolated, but preferably it is converted directly with 2-thienyllithium to the corresponding thienylethylamine of the formula:

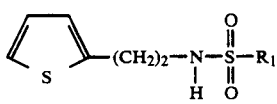
(III)

wherein $R_1$ has the above-mentioned meaning.

The 2-thienyllithium can be produced in a known way, e.g., according to Chadwick et al., J. Chem. Soc., Perkin I, 1977, P. 887 from thiophene and e.g., butyllithium in a suitable solvent, preferably at the same time and parallel with the first step of the process according to the invention, and is added to the second step.

The reaction with 2-thienyllithium advantageously takes place in the same solvent as the first step at a temperature between −80° and +60° C.

The resultant thienylethylamine of the formula:

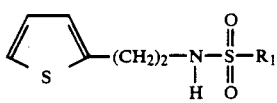
(III)

wherein $R_1$ has the above-mentioned meaning, is again advantageously not isolated but is mixed directly with the reactants of the following step compounds of formula RX. In these compounds, R has the above-mentioned meaning, while X is a chlorine, bromine or iodine atom. Suitable representatives of the compounds RX are, for example, acetylchloride, benzoylchloride, benzylchloride or o-chlorobenzylchloride. As the solvent, it is advantageous to take over the one from the precursor. But also one can replace the solvent with a polar solvent. The operation at the reaction temperature is suitably between −50° and +100° C. If R in the compound RX is benzyl or o-chlorobenzyl, the reaction temperature is preferably between +20° and +100° C.; with R being acetyl or benzoyl, it is preferably between −10° and +20° C. After the reaction is completed, the target product is isolated and purified in the usual way.

DETAILED DESCRIPTION OF THE INVENTION

EXAMPLE 1

Production of N-[(2-chlorophenyl)methyl]-4-methyl-N-[2-(2-thienyl)ethyl]-benzosulfonamide (a) Production of N-[(4-methylohenyl)sulfonyl]-aziridine 118 mg (3 mmol) of sodium hydride (55 percent in oil) was placed in 3 ml of tetrahydrofuran and cooled to 0° C. 1 g (2.7 mmol) of N,O-bis-(toluenesulfonyl)-ethanolamine in 2 ml of tetrahydrofuran was added in 7 minutes (generation of gas). The reaction mixture was warmed to room temperature. Then 2 ml of ether was added and it was stirred for 50 minutes at room temperature.

(b) Production of 2-thienyllithium 228 mg (27 mmol) of thiophene and 315 mg (2.7 mmol) of tetramethylethylenediamine were placed in 3 ml of ether at room temperature. Then 1.1 ml (2.7 mmol) of butyllithium (2.5 M in hexane) was added within 2 minutes (exothermic). It was allowed to stir for 30 minutes more at room temperature.

(c) Production of 4-methyl-N-[2(2-thienyl)ethyl]-benzenesulfonamide

The reaction mixture from step (b) was then added, at room temperature within 3 minutes, to the reaction mixture from step (a). The 3 ml of tetrahydrofuran was added to make the suspension better stirrable. It was allowed to stir for 40 minutes at room temperature.

(d) Production of N-[(2-chlorophenyl)methyl]-4-methyl-N-[2,(2-thienyl)ethyl]-benzenesulfonamide 654 mg (4.05 mmol) of 2-chlorobenzylchloride was added to the reaction mixture from step (c). The reaction mixture was then refluxed. It was allowed to stir at reflux temperature (62° C.) for 4 hours. After cooling to room temperature, 20 ml of water was added. The tetrahydrofuran was removed in a vacuum. The aqueous residue was extracted 3 times with 15 ml of methylene chloride each. The organic phase was separated, dried with magnesium sulfate and then concentrated by evaporation. Thus, a dark oil resulted, from which the product crystallized. The yield was 860 mg of N-[(2-chlorophenyl)methyl]-4-methyl-N-[2-(2-thienyl)ethyl]benzenesulfonamide, which is 78 percent. The melting point of the product was 95.5°–96.5° C. Other data for the product was:

$^1$H-NMR: (CDCl$_3$, 300 MHz) δ in ppm 7.75, d, J=8.5 Hz, 2H; 7.55, dd, J=7 Hz, 2.5 Hz, 1H; 7.37–7.31, m, 3H; 7.30–7.20, m, 2H; 7.08, d, J=3.5 Hz, 1H; 6.87, dd, J=5 Hz, 3.5 Hz, 1H; 6.68, d, J=3.5 Hz, 1H; 4.51, s, 2H; 3.40, dd, J=8 Hz, 8 Hz, 2H; 2.88, dd, J=8 Hz, 8 Hz, 2H; 2.45, s, 3H.

EXAMPLE 2

The production of a 4,5,6,7-tetrahydrothieno-[2,3c]-pyridine from a substituted thienylethylamine of the invention (a) Production of N-[(2-chlorophenyl)methyl]-2[(2-thienyl)ethylamine]-hydrochloride (first step).

A mixture of 0.2 g of N-[(2-chlorophenyl)methyl]-4-methyl-N-[2-(2-thienyl)ethyl]-benzosulfonamide (0.5 m mole), 0.4 g of phenol (4.3 m mole) and 3 ml of a 48 percent aqueous HBr solution was heated at 100° C. during 45 minutes, after which 100 ml of ether and 5 ml of water were added. The two phases were separated and the aqueous phase was 3 times extracted with 20 ml ether. Then, the acidified aqueous phase was made alkaline with a 20 percent aqueous NaOH solution and was then 3 times extracted with 20 ml of ether. The combined ether phases were dried over MgSO$_4$ and concentrated to give 35.5 mg (yield: 30 percent of a yellow oil).

(b) Production of 5-[(2-chlorophenyl)methyl]-4,5,6,7-tetrahydrothieno[3,2-c]pyridine (second step).

15 g (0.052 mole) of the compound obtained in (a), 100 ml of water and 5 ml of a 35 percent aqueous formaldehyde solution (0.58 mole) were heated at 90° C. during 15 minutes, after which 2N hydrochloric acid (100 ml) was added thereto and the resultant mixture was heated at 90° C. during 1.5 hours. After cooling, a slight precipitate was removed by filtration. The aqueous phase was made alkaline with 2N NaOH and was then extracted with 350 ml of diisopropyl ether. The organic phase was washed with water, dried over sodium sulfate and concentrated, to give 11.32 g of a light organic oil. This oil was then dissolved in isopropyl ether and, after the addition of dry HCl, 10 g of a hydrochloride was precipitated which was purified by recrystallization from boiling absolute ethanol (yield: 64 percent).

What is claimed is:

1. Process for the production of a substituted thienylethylamine of the formula:

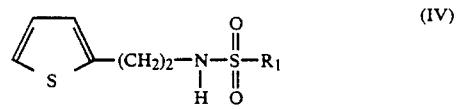

wherein R is formyl, acetyl or benzoyl or is benzyl, which is ring-substituted by at least one halogen atom, and R$_1$ is lower alkyl, phenyl or substituted phenyl, comprising: converting a substituted ethanolamine of the formula:

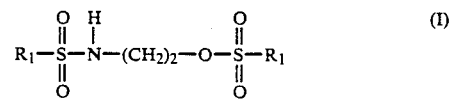

wherein R$_1$ has the above-mentioned meaning, with a strong base to an aziridine of the formula:

wherein R$_1$ has the above-mentioned meaning, converting the aziridine of formula (II) with 2-thienyllithium to a thienylethylamine of the formula:

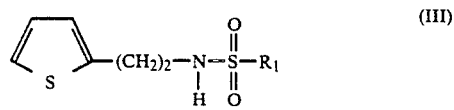

wherein R$_1$ has the above-mentioned meaning, and converting the thienylethylamine of formula (III) with a compound RX, wherein R has the above-mentioned meaning and X is chlorine, bromine or iodine, to the thienylethylamine of formula (IV).

2. Process according to claim 1 wherein an alkali hydride, alkali amide or alkyllithium is used as the strong base.

3. Process according claim, 1 or 2 wherein the conversion to the aziridine takes place at a temperature between −80 and +100° C. in an inert solvent.

4. Process according to claim 1 wherein the reaction with 2-thienyllithium takes place at a temperature between −80° and +60° C. in an inert solvent.

5. Process according to claim 1 wherein the reaction with the compound RX takes place at a temperature between −50° and +100° C.

6. Process according to claim 1 wherein the process takes place without isolation of the intermediate products.

* * * * *